(12) United States Patent
Li et al.

(10) Patent No.: US 7,623,972 B1
(45) Date of Patent: Nov. 24, 2009

(54) DETECTION OF PRESENCE OF CHEMICAL PRECURSORS

(75) Inventors: Jing Li, San Jose, CA (US); Meyya Meyyappan, San Jose, CA (US); Yijiang Lu, San Jose, CA (US)

(73) Assignee: The United States of America as represented by the Administrator of the National Aeronautics and Space Administration, Washington, DC (US)

( * ) Notice: Subject to any disclaimer, the term of this patent is extended or adjusted under 35 U.S.C. 154(b) by 0 days.

(21) Appl. No.: 11/591,630

(22) Filed: Oct. 31, 2006

Related U.S. Application Data

(63) Continuation-in-part of application No. 11/178,079, filed on Jul. 8, 2005.

(51) Int. Cl.
*G01N 31/00* (2006.01)
*G01N 27/00* (2006.01)
*G06F 19/00* (2006.01)

(52) U.S. Cl. .................... 702/27; 422/83; 977/953; 977/957

(58) Field of Classification Search ............ 702/27; 977/953, 957; 422/83
See application file for complete search history.

(56) References Cited

U.S. PATENT DOCUMENTS

| | | | |
|---|---|---|---|
| 6,289,328 B2 * | 9/2001 | Shaffer ..................... 706/20 |
| 6,528,020 B1 | 3/2003 | Dai et al. | |
| 6,537,498 B1 * | 3/2003 | Lewis et al. .............. 422/82.01 |
| 7,312,095 B1 * | 12/2007 | Gabriel et al. ............... 438/49 |
| 7,318,908 B1 * | 1/2008 | Dai ........................... 422/68.1 |
| 2003/0175161 A1 | 9/2003 | Gabriel et al. | |
| 2005/0126913 A1 | 6/2005 | Burke et al. | |
| 2005/0169798 A1 * | 8/2005 | Bradley et al. ............... 422/57 |

OTHER PUBLICATIONS

Li, et al., Nano Chemical Sensors With Polymer-Coated Carbon Nanotubes, IEEE Sensors Journal, Oct. 5, 2006, 1047-1051, 6-5, IEEE.
Lu, et al., Room temperature methane detection using palladium loaded single-walled carbon nanotube sensors, Chemical Physics Letters, 2004, 344-348, 391, Elsevier B.V.
Lu, et al., A carbon nanotube sensor array for sensitive gas discrimination using principal component analysis, Journal of Electroanalytical Chemistry, 2006, 105-110, 593, Elsevier B.V.

(Continued)

*Primary Examiner*—Eliseo Ramos Feliciano
*Assistant Examiner*—Janet L Suglo
(74) *Attorney, Agent, or Firm*—John F. Schipper; Robert M. Padilla

(57) ABSTRACT

Methods and systems for determining if one or more target molecules are present in a gas, by exposing a functionalized carbon nanostructure (CNS) to the gas and measuring an electrical parameter value $EPV(n)$ associated with each of N CNS sub-arrays. In a first embodiment, a most-probable concentration value $C(opt)$ is estimated, and an error value, depending upon differences between the measured values $EPV(n)$ and corresponding values $EPV(n;C(opt))$ is computed. If the error value is less than a first error threshold value, the system interprets this as indicating that the target molecule is present in a concentration $C \approx C(opt)$. A second embodiment uses extensive statistical and vector space analysis to estimate target molecule concentration.

6 Claims, 7 Drawing Sheets

OTHER PUBLICATIONS

Matthews, et al., Effects of Electrode Configuration on Polymer Carbon-Black Composite Chemical Vapor Sensor Performance, IEEE Sensors Journal, Jun. 2002, 160-168, 2-3, IEEE.

Young, et al., High-Sensitivity NO2 Detection with Carbon Nanotube—Gold Nanoparticle Composite Films, Journal of Nanoscience and Nanotechnology, 2005, 1509-1513, 5, American Scientific Publishers, USA.

Li, et al., Carbon Nanotube Sensors for Gas and Organic Vapor Detection, Nano Letters, 2003, 929-933, 3-7.

Li, et al., A Gas Sensor Array Using Carbon Nanotubes and Microfabricatio . . . , Electrochemical and Solid-State Letters, 2005, H100-H102, 8, The Electrochemical Society, Inc.

Applicant's response to an Office Action in related, U.S. Appl. No. 11/178,079, filed Jul. 8, 2005, Office Action mailed Oct. 29, 2008.

Final Rejection in related case, mailing date May 28, 2009, U.S. Appl. No. 11/178,079, Filing date: Jul. 8, 2005.

First Office Action in related case, mailing date May 29, 2009, U.S. Appl. No. 11/489,803, Application filing date: Jul. 12, 2006.

Calusdian, et al., Design and Testing of a Wireless Portable Carbon Nanotube-Based Chemical Sensor System, Sixth IEEE Conference on Nanotechnology, Jun. 17-20, 2006, 794-797.

First Office Action in related case, mailed Sep. 4, 2009, U.S. Appl. No. 11/416,505, filed Apr. 28, 2006.

Shaffer, et al., A comparison study of chemical sensor array pattern recognition algorithms, Analytica Chimica Acta 384, 1999, 305-317, Elsevier.

* cited by examiner

DETECTION OF PRESENCE OF CHEMICAL PRECURSORS

ORIGIN OF THE INVENTION

This application is a continuation-in-part of a prior-filed application, U.S. Ser. No. 11/178,079, filed 8 Jul. 2005.

FIELD OF THE INVENTION

This invention relates to use of functionalized carbon nanostructures to detect presence of one or more chemical precursors for a target molecule.

BACKGROUND OF THE INVENTION

Certain selected chemicals associated with terrorist activities are too unstable to be prepared in a final form. These selected chemicals are often prepared as precursor components, to be combined at a time immediately preceding a time of application of the selected chemical. An example is a liquid explosive, which usually requires provision of an oxidizer, an energy source and a chemical or physical mechanism to combine the other components at a time immediately preceding detonation. Detection of presence of the oxidizer (e.g., $H_2O_2$) or the energy source (e.g., nitromethane) is often possible but must be performed in a short time interval (e.g., 5-15 sec) and in an environment with a very small concentration (e.g., 1-100 ppm), because the target chemical(s) is present in a sealed container.

What is needed is a system that allows detection of presence of a target oxidizer and/or a target energizer in small concentrations (as small as 1 ppm) in a relatively small time interval, preferably no more than about 5-15 sec. Preferably, the system should allow detection of at least one oxidizer and of at least one energizer, substantially simultaneously, should operate with a relatively small "footprint" in a real life environment, and should operate with only a small energy expenditure.

SUMMARY OF THE INVENTION

These needs are met by the invention, which provides a system and associated method for detecting one or more chemical precursors (components) of a multi-component compound that may become unstable when fully assembled or combined. First and second carbon nanostructures ("CNSs") are loaded (by doping, impregnation, coating or other functionalization process) with different first and second chemical substances that react with first and second chemical precursors, respectively, which may be the same or may be different, if these precursors are present in a gas to which the CNSs are exposed. After exposure to the gas, a measured electrical parameter value EPV (e.g., impedance, conductivity, capacitance, inductance, etc.) changes with time in a predictable manner, if a selected chemical precursor is present, and will approach an asymptotic value promptly after exposure to the precursor. The measured EPVs are compared with one or more sequences of reference EPVs for one or more known target precursor molecules, and a most probable concentration value is estimated for each of one, two or more target molecules. An error value is computed, based on differences for the measured and reference EPVs using the most probable concentration values. Where the error value is less than an error value threshold, the system concludes that the target molecule is likely. Presence of one, two or more target molecules in the gas can be sensed from a single set of measurements.

DESCRIPTION OF BEST MODE OF THE INVENTION

Figure 1:
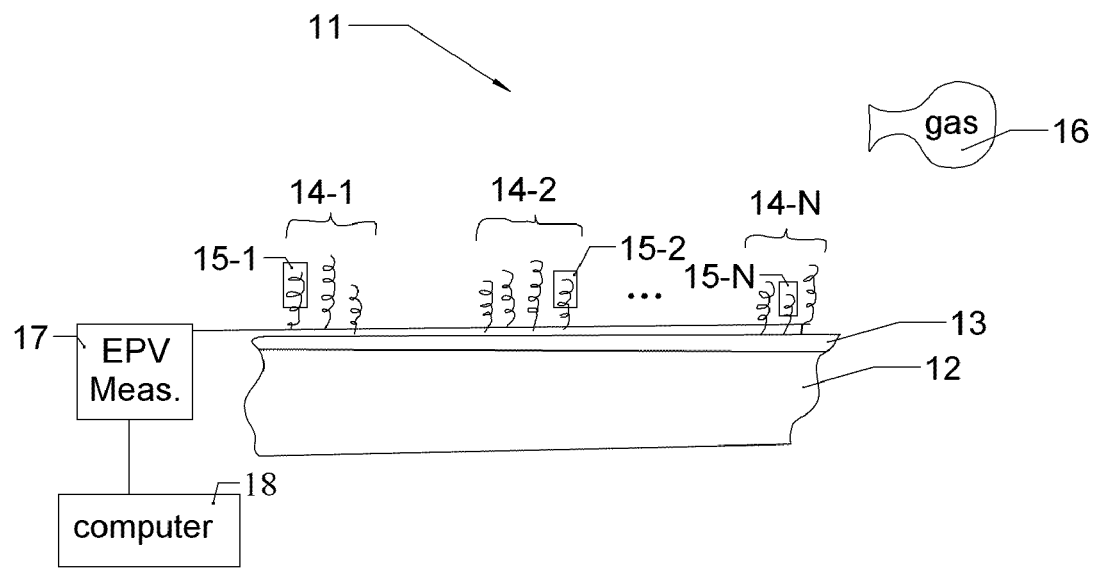
FIG. 1 schematically illustrates a system for practicing the invention.

FIG. 1 schematically illustrates a system 11 for practicing the invention. The system 11 includes: a substrate 12; an appropriate catalyst underlayer 13; a sequence of sub arrays 14-$n$ of carbon nanostructures ("CNSs") grown on the catalyzed substrate; a selected loading (doping, impregnation, coating, etc.) 15-$n$ of the CNS sub-array 14-$n$; a source 16 of a gas to be interrogated; a measurement mechanism 17 for measuring an electrical parameter value EPV(n) (impedance, conductance, capacitance, etc.) at each of the sequence of CNS sub-arrays, before and after exposure of that sub-array to the gas; and a computer 18 programmed to receive the sequence of measured electrical parameter values EPV(n), to compare the measured EPV(n) with a corresponding reference values EPV(n;ref), and to estimate whether a target molecule is likely present in the gas in a most probable concentration value. Each CNS sub-array 14-$n$ may consist of a single CNS or may include two or more CNSs, and two different CNS sub-arrays, 14-$n$ and 14-$n'$, may have the same number, or a different number, of CNSs. The particular electrical parameter value EPV measured for each of the functionalized sensors may be electrical impedance, electrical conductance, capacitance, inductance or some other relevant, measurable electrical value.

Figure 2:
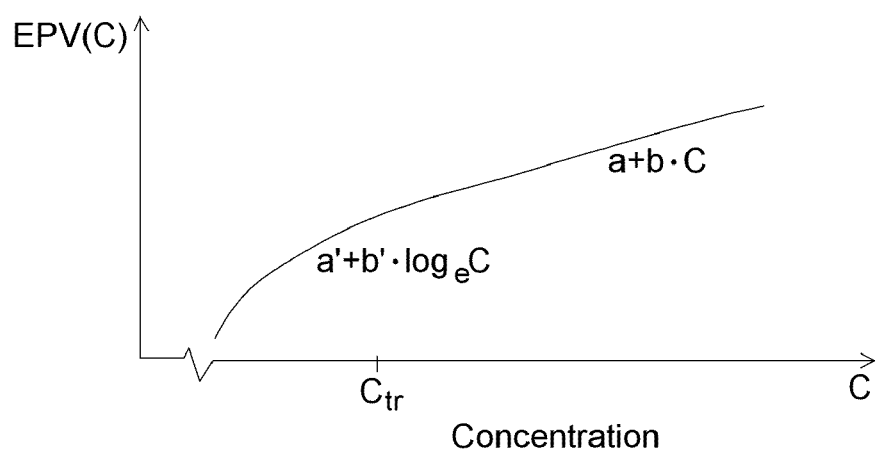
FIG. 2 graphically illustrates different concentration regimes.

For relatively large concentrations, it is assumed that the measured EPV for a given target molecule will vary linearly with the concentration C, $$\text{EPV}(C) = a + b \cdot C, \quad (1)$$

where the parameters a and b are characteristic of the particular target molecule for which the measurements are made. Where $\text{EPV}(C_{1,1})$ and $\text{EPV}(C_{1,2})$ are values for a pure substance measured at the different concentration values $C_{1,1}$ and $C_{1,2}$, respectively, the parameter values a and b can be estimated by $$a = \{\text{EPV}(C_{1,1})C_{1,2} - \text{EPV}(C_{1,2})C_{1,1}\}/\{C_{1,2} - C_{1,1}\}, \quad (2\text{-}1)$$

$$b = \{\text{EPV}(C_{1,1}) - \text{EPV}(C_{1,2})\}/\{C_{1,2} - C_{1,1}\}, \quad (2\text{-}2)$$

for each target molecule. For smaller concentrations ($\approx$5-50 ppm), it may be preferable to use a logarithmic approximation, $$\text{EPV}(C) = a' + b' \cdot \log_e C, \quad (3)$$

where a' and b' are selected parameters. The parameter values a' and b' can be determined in a manner similar to that of Eqs. (2-1) and (2-2), by replacing the variables $C_{1,1}$ and $C_{1,2}$ by $\log_e\{C_{1,1}\}$ and $\log_e\{C_{1,2}\}$, respectively. FIG. 2 graphically illustrates the two concentration regimes for EPV(C), corresponding to Eqs. (1) and (3), which join together at a concentration transition value $C_{tr}$ for which $$a'+b'\cdot\log_e C_{tr}=a+b\cdot C_{tr}. \quad (4)$$

Given an array of N sub-arrays of CNS sensors and a set of K target molecules (k=1, . . . , K; K≧2), the EPV data for the sensors can be pre-processed in order to identify more clearly which CNS sensor sub-arrays are more sensitive to presence of a particular target molecule. In a first embodiment, the array is exposed to a selected target molecule, such as $H_2O_2$, at a selected sequence $\{C_q\}_q$ (q=1, . . . , Q with Q=N) known (not necessarily distinct) concentration values (e.g., 500 ppm, 14,000 ppm, 65 ppm, 1200 ppm, 10 ppm, etc.), and a reference measurement value EPV(n;q;k;ref) (n=1, 2, . . . , N) is recorded for each sensor sub-array n, each concentration $C_q$ of a reference gas containing a selected target molecule (k). Measurements for one or more concentration values for the selected target molecule gas can be repeated, if desired, to obtain an N×N square matrix of values. With q fixed, an N×N matrix $\{EPV(n;q;k;ref)/EPV(n;k;norm)\}=E(n;q;k;ref)$ is formed, where, EPV(n;k;norm) is a normalization factor for the selected target molecule gas no. k and the sub-array no. n, which may be chosen as $$EPV(n; k; norm) = \left\{ \sum_{q=1}^{N} u_q EPV(n; q; k; ref)^\rho \right\}^{1/\rho}, \quad (5)$$

where $\{u_q\}_q$ is a selected set of non-negative weight numbers whose sum is a selected positive number (e.g., 1 or N) and $\rho$ is a selected positive number. The normalization factor E(n; k;norm) may be a single EPV (e.g., $u_{q1}=1$ and $u_q=0$ for q≠q1), or may be a weighted sum of two or more EPVs. This normalization (optional) is intended to compensate for the concentration dependence of the particular target molecule.

For each sub-array n (fixed), the mean and standard deviation for each of K reference gases, numbered k=1, . . . , K (K≧2) are computed, as $$\mu(n; k) = \sum_{q=1}^{N} E(n; q; k; ref)/N, \quad (6A)$$

$$\mu(n) = \sum_{k=1}^{K} \mu(n; k)/K, \quad (6B)$$

$$\sigma(n; k) = \left\{ \sum_{q=1}^{N} \{E(n; q; k; ref) - \mu(n; k)\}^2 / N \right\}^{1/2}, \quad (7A)$$

$$\sigma(n) = \sum_{q=1}^{N} \sigma(n; k)/K. \quad (7B)$$

One now forms K autoscaled N×N matrices, defined by $$S(n;q;k)=\{E(n;q;k;ref)-\mu(n)\}/\sigma(n), \quad (8\text{-}k)$$

and analyzes K eigenvalue equations $$S(n;q;k)V(k;\lambda(k))=\lambda(k)V(k;\lambda(k)), \quad (9\text{-}k)$$

where k (=1, . . . , K) is fixed and $V(k;\lambda(k))$ is a normalized N×1 vector that will usually depend upon the reference gas (k). If, as is likely, the N eigenvalues $\lambda(k)$ for a fixed reference gas k are distinct, the corresponding eigenvectors $V(k;\lambda(k))$ are mutually orthogonal (non-degeneracy). In the unusual event (degeneracy) that two or more of the N eigenvalues $\lambda(k)$ are equal, different non-zero linear combinations of the corresponding eigenvectors $V(k;\lambda(k))$ can be constructed that are orthogonal to each other, within a sub-space spanned by the reduced set of eigenvectors corresponding to the identical eigenvalues.

Each matrix equation (9-k) has a sequence of N (eigenvalue; eigenvector) pairs, $\{(\lambda_n(k);V_n(k;\lambda_q(k))\}_n$, for a fixed reference gas k, and it is assumed here that the eigenvalues are arranged so that $$|\lambda_1(k)|\geq|\lambda_2(k)|\geq \ldots \geq|\lambda_N(k)| \quad (10\text{-}k)$$

and so that the highest magnitude eigenvalue in each set satisfies $$|\lambda_1(k1)|\geq|\lambda_1(k2)|\geq \ldots |\lambda_1(kN)|, \quad (11)$$

where $\{k1, k2, \ldots, kN\}$ includes each of the integers $\{1, 2, \ldots, N\}$ precisely once.

The eigenvector $V(k1;\lambda_1(k1))$ is identified as a first basis vector V'(1):

$$V'(k1;\lambda_1(k1))=V(k1;\lambda_1(k1)) \quad (12\text{-}1)$$

A second modified vector $$V'(k2;\lambda_1(k2))=V(k2;\lambda_1(k2))-\{V(k2;\lambda_1(k2)),V'(k1;\lambda_1(k1))\}V'(k1;\lambda_1(k1)) \quad (12\text{-}2)$$

is computed, where $\{V(k2;\lambda_2(k2)),V'(1)\}$ is the scalar product (also referred to as the inner product) of the vectors $V(k2;\lambda_2(k2))$ and V'(k1). More generally, a pth modified vector $$V'(kp; \lambda_1(kp)) = V(kp; \lambda_1(kp)) - \sum_{r=1}^{p-1} \{V(kp; \lambda_1(kp)), V'(kr; \lambda_1(kr))\} V'(kr; \lambda_1(kr)) \quad (12-p)$$

is computed for p=2, . . . , K. The set of vectors $\{V'(kr;\lambda_1(kr))\}_k$ (r=1, . . . , K) is mutually orthogonal, in the sense that the scalar products satisfy $$\{V'(kr; \lambda_1(kr)), V'(ks; \lambda_1(ks))\} = \delta_{r,s}. \quad (13)$$

$$> 0 (r = s)$$

$$= 0 (r \neq s).$$

Each of the set of vectors $\{V'(kr;\lambda_1(kr))\}_r$ (r=1, . . . , K) is maximally independent of each of the other vectors in the set, in the sense of mutual orthonormality (Eq. (13)). Each vector $V'(kr;\lambda_1(kr))$ will have relatively large (primary) contributions from some of the sensor sub-arrays and will have smaller (secondary) contributions from the remainder of the N sub-arrays. The vectors $V'(kr;\lambda_1(kr))$ identify a maximally independent set of linear combinations of EPV responses from the N sub-arrays that can be used to distinguish presence of one reference gas (target molecule kr) from presence of another reference gas (target molecule ks). For example, if the set of reference gases are $H_2O_2$, $H_2O$ and $CH_3OH$, N=3 and three matrix eigenvalue equations are to be solved in Eqs. (9-k) (k=1, 2, 3). More generally, presence or absence of any of K target molecules (K≧2) may be estimated.

The linear combinations LC(kp) of EPV measurements for the different sensor sub-arrays correspond to modified principal components for the particular reference gases chosen. Choice of another set of another set of reference gases will result in a different set of modified principal components, although change of one or more concentration values within a reference gas may have little or no effect on the modified principal components.

Figure 3A:
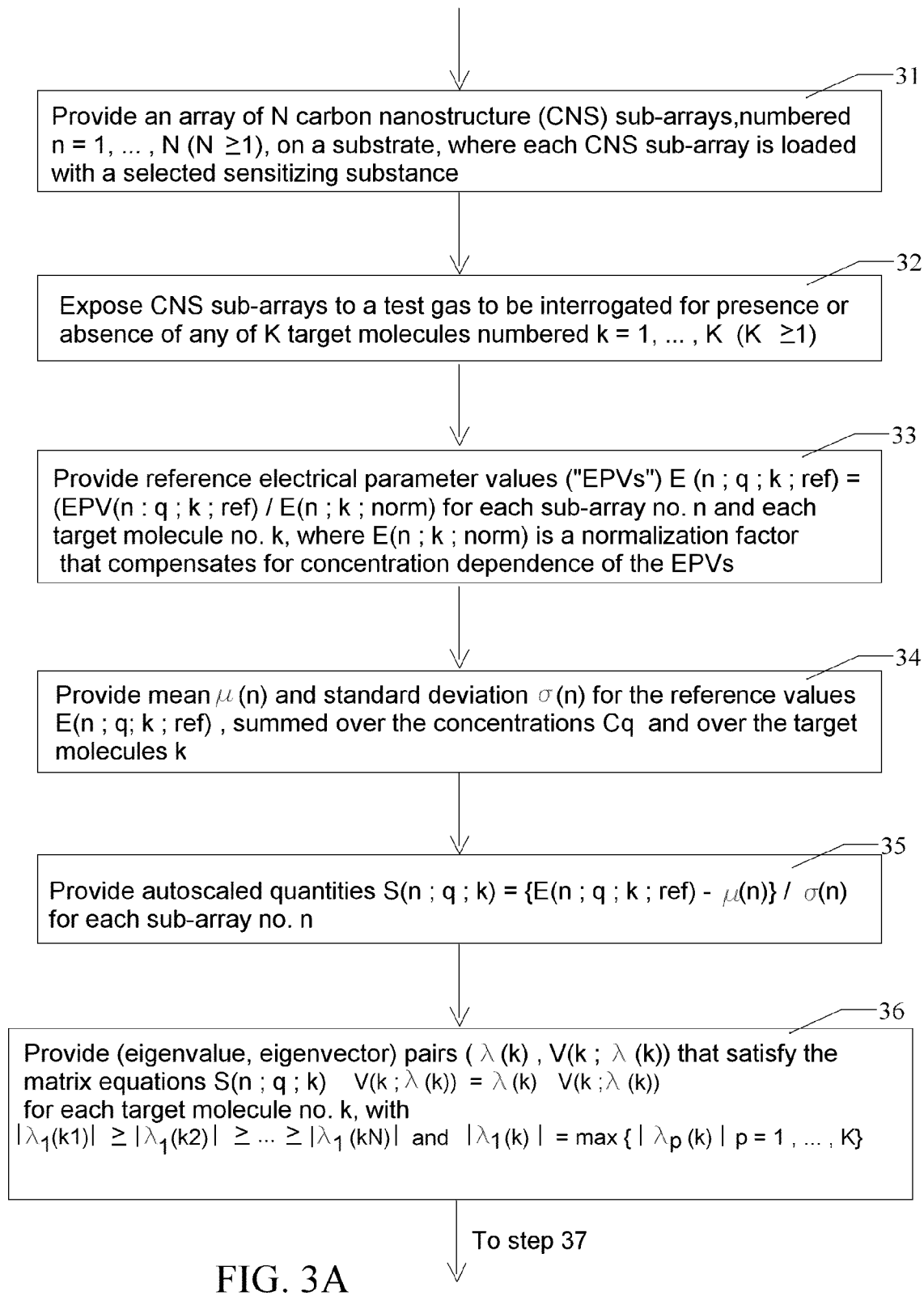
FIGS. 3 and 4 are flow chart of procedures for practicing the invention.
Figure 3B:
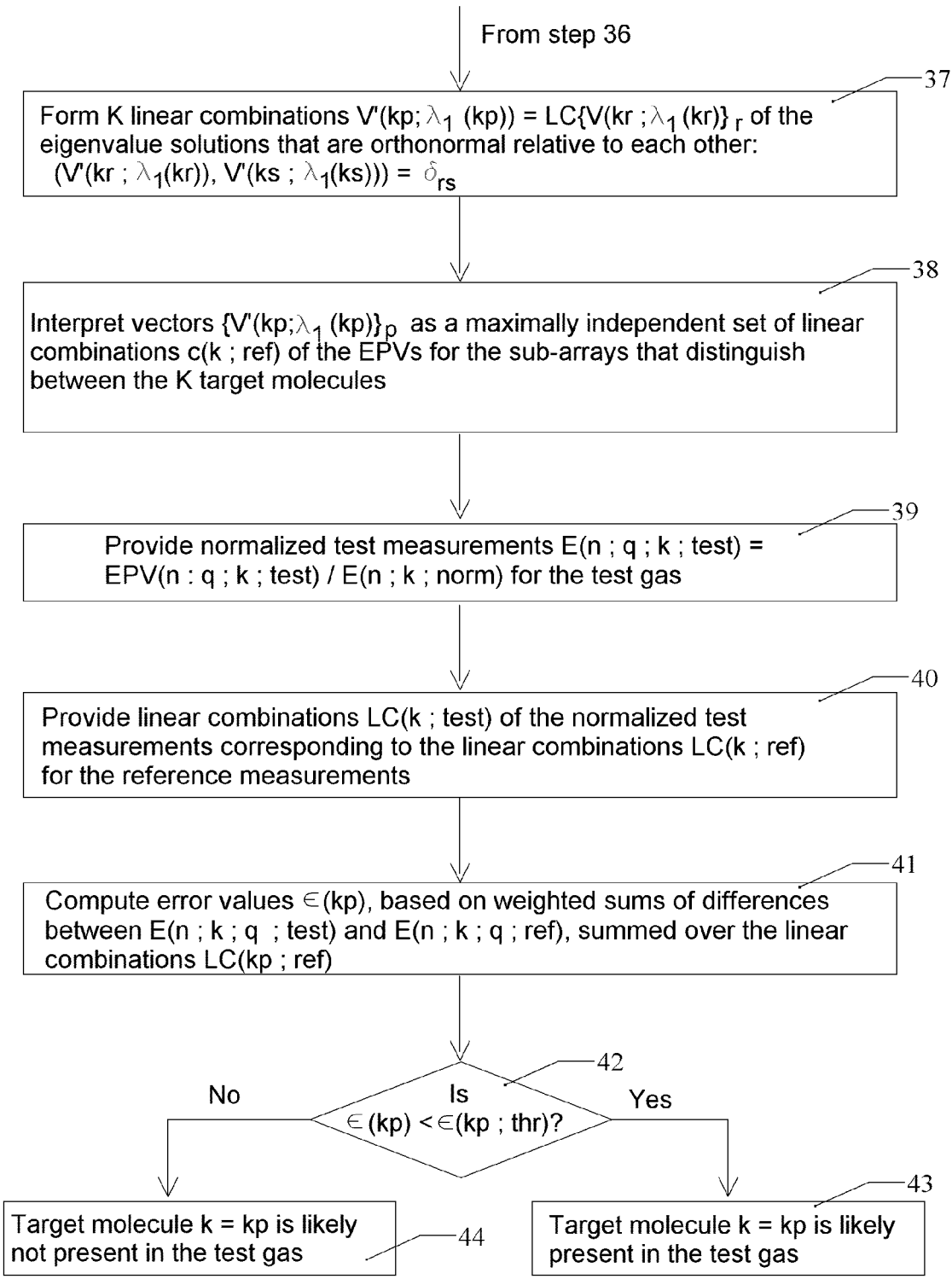

FIG. 3 is a flow chart of a procedure for practicing the first embodiment. In step 31, N sub-arrays (N≧2) of carbon nanostructures ("CNSs"), numbered n=1, ..., N, are provided on a substrate, where each CNS sub-array is doped, coated, impregnated or otherwise functionalized ("loaded") with a selected sensitizing substance drawn from a group of substances, for example, Au nanoparticles, associated with other particles. In step 32, the CNS sub-arrays are exposed to a test gas to be interrogated (for presence or absence of K different target molecules, with K≧1). In step 33, reference electrical parameter values E(n;q;k;ref)=(EPV(n;q;k;ref)/EPV(n;k;norm) are provided for each CNS sub-array no. n, for each of a selected sequence of K target molecules (K≧1), and for each of a selected sequence of concentrations Cq of the target molecules (q=1, ..., N). Here, EPV(n;k;norm) is a normalization factor that compensates for dependence of an EPV upon concentration of a target molecule.

In step 34, means μ(n) and standard deviations σ(n) for the reference values E(n;q;k), summed over the concentration index q and over the target molecule index k, are provided. In step 35, autoscaled quantities $$S(n;q;k) = \{E(n;q;k;ref) - \mu(n)\}/(\sigma(n)), \quad (8\text{-}k)$$

are provided. In step 36, (eigenvalue;eigenvector) pairs (λ(k); V(k;λ(k))) are provided that satisfy the matrix equations $$S(n;q;k)V(k;\lambda(k)) = \lambda(k)V(k;\lambda(k)). \quad (9\text{-}k)$$

The eigenvalues are assumed to be (re)arranged so that $$|\lambda_1(k)| \geq |\lambda_2(k)| \geq \ldots \geq |\lambda_N(k)| \, (k=1, \ldots, K) \quad (10\text{-}k)$$

and so that the highest magnitude eigenvalue in each set satisfies $$|\lambda_1(k1)| \geq |\lambda_1(k2)| \geq \ldots \geq |\lambda_1(kN)|, \quad (11)$$

where $\{k1, k2, \ldots, kN\}$ includes each of the integers $\{1, 2, \ldots, N\}$ precisely once.

In step 37, K linear combinations V'(kp;λ(kp))=LC{V(kr;λ(kr))}=LC(kp) of the eigenvectors are formed so that a selected eigenvectors V'(kr;λ$_1$(kr)) are orthogonal to each other, in the sense of Eq. (13). This step may be implemented, for example, using an orthogonolization process set forth in Eqs. (12-1) through (12-p), or by any other suitable process. In step 38, the vectors $\{V'(kp;\lambda_1(kp))\}_p$ are interpreted as a maximally independent set of linear combinations of the EPVs for the N sub-arrays that distinguish between the K target molecules. Steps 39-44 (optional) enhance this embodiment by estimating whether a target molecule is likely to be present in a test gas.

In step 39, normalized test measurements EPV(n;q;k;test)/EPV(n;k;norm)=E(n;q;k;test) are provided for the (unknown) gas of interest. In step 40, linear combinations LC(kp;test) of these measurements corresponding to the linear combinations LC(kp;ref) of the N sub-arrays for the vectors $\{V'(kp;\lambda_1(kp))\}_p$ are provided. In step 41, error values $$\epsilon(kp) = \Sigma e_n |E(n;q;kp;test) - E(n;q;kp;ref)|^s,$$

$$LC(kp;ref) \quad (14)$$

are computed, where "LC(kp;ref)" indicates a weighted sum ($w_n$) over the linear combination of sensor sub-array indices (n) corresponding to the vector combination V'(kp;λ$_1$(kp)) in Eq. (12-p) (p=1, ..., K) and s is a selected positive number. In step 42, the error value ε(kp) is compared with a selected positive error threshold value ε(kp;thr), for at least one value of p=1, ..., K. When ε(kp) is less than ε(kp;thr), the system interprets this condition as indicating that a target molecule, corresponding to the linear combination LC(kp) of sub-array measurement values is likely to be present in the test gas, in step 43. When ε(kp) is at least equal to ε(kp;thr), the system interprets this condition as indicating that a target molecule, corresponding to the linear combination LC(kp) of sub-array measurement values is not likely to be present in the test gas, in step 44.

In a second embodiment, illustrated for convenience here for first and second target molecules (K=2), each of the N CNS sensor sub-arrays is loaded (doped, impregnated, coated, or otherwise functionalized) with a different functionalizing substance FS, with each FS being chosen so that, for different first and second target molecules, at least one of the CNS sensor sub-arrays CNS no. n will produce substantially different EPV measurements for the first and second target molecules. Where conductance is the EPV of interest, the CNS loading substances FS may, for example, be Au nanoparticles with associated side groups.

Most probable concentrations, C1(opt) and C2(opt), for the first and second target molecules present are computed using the approximations for concentration dependence set forth in Eqs. (1) and (3). For concentrations C1 and C2 above the transition values, C1$_{tr}$ and C2$_{tr}$, a compound error value $$\varepsilon(C1; C2) = \sum_{n=1}^{N} w'_n |EPV(n) - \{a_n(1) + b_n(1) \cdot C1\} - \{a_n(2) + b_n(2) \cdot C2\}|^p, \quad (15)$$

is computed, where $\{a_n(1), b_n(1)$ and $(a_n(2), b_n(2)\}$ are the parameter pairs (assumed known through experiment) that appear in Eq. (1) for the concentration dependence of the EPVs for the CNS sub-array no. n (n=1, ..., N), w'$_n$ is a weighting number for the CNS sub-array number n, and p is a selected positive number. The weighting numbers w'$_n$ may be equal or may reflect the relative number of CNSs in each of the sub-arrays. Compound error value in Eq. (15) is minimized with respect to choices of the (unknown) concentrations C1 and C2:

$$\partial\{\epsilon(C1;C2)\}/\partial C1 = 0 \text{ at } (C1,C2) = (C1(opt),C2(opt)) \quad (16\text{-}1)$$

$$\partial\{\epsilon(C1;C2)\}/\partial C2 = 0, \text{ at } (C1,C2) = (C1(opt),C2(opt)) \quad (16\text{-}2)$$

Using the linear concentration dependence from Eq. (1) for each of the target molecules 1 and 2, Eqs. (16-1) and (16-2) can be re-expressed as a first set of coupled relations in the optimum values, C1=C1(opt) and C2=C2(opt), $$\sum_{n=1}^{N} w'_n b_n^2 C1 + \sum_{n=1}^{N} w'_n b_n b'_n C2 = \sum_{n=1}^{N} w'_n \{EPV(n) - a_n - a'_n\} b_n, \quad (17\text{-}1)$$

$$\sum_{n=1}^{N} w'_n b_n b'_n C1 + \sum_{n=1}^{N} w'_n b'^2_n C2 = \sum_{n=1}^{N} w'_n \{EPV(n) - a_n - a'_n\} b'_n. \quad (17\text{-}2)$$

Using the linear concentration dependence from Eq. (1) for target molecule 1 and the logarithmic concentration dependence from Eq. (3) for the target molecule 2, Eqs. (16-1) and (16-2) can be re-expressed as a third set of coupled relations in the optimum values, C1=C1(opt) and C2=C2(opt), $$\sum_{n=1}^{N} w'_n b_n^2 C1 + \sum_{n=1}^{N} w'_n b_n b'_n \log_e C2 = \sum_{n=1}^{N} w'_n \{EPV(n) - a_n - a'_n\} b_n, \quad (17-3)$$

$$\sum_{n=1}^{N} w'_n b_n b'_n C1 + \sum_{n=1}^{N} w'_n b'^2_n \log_e C2 = \sum_{n=1}^{N} w'_n \{EPV(n) - a_n - a'_n\} b'_n, \quad (17-4)$$

where a common factor of C2 for all terms in Eq. (8-4) has been canceled.

Using the logarithmic concentration dependence from Eq. (3) for the target molecules 1 and 2, Eqs. (16-1) and (16-2) can be re-expressed as a second set of coupled relations in the optimum values, C1=C1(opt) and C2 C2(opt), $$\sum_{n=1}^{N} w'_n b_n^2 \log_e C1 + \sum_{n=1}^{N} w'_n b_n b'_n \log_e C2 = \quad (17-5)$$
$$\sum_{n=1}^{N} w'_n \{EPV(n) - a_n - a'_n\} b_n,$$

$$\sum_{n=1}^{N} w'_n b_n b'_n \log_e C1 + \sum_{n=1}^{N} w'_n b'^2_n \log_e C2 = \quad (17-6)$$
$$\sum_{n=1}^{N} w'_n \{EPV(n) - a_n - a'_n\} b'_n,$$

The equation pair (17-1) and (17-2) is formally similar to the equation pair (17-5) and (17-6) so that the same well known algebraic methods can be used to formally determine the respective solution pairs (C1,C2) and ($\log_e C1, \log_e C2$).

Equations (17-1) through (17-6) extend, in an obvious manner, to K≧3 different target molecules, where the EPV of each target molecule and each CNS sub-array (n) is represented, in the appropriate concentration range, by Eq. (1) or Eq. (3). Where K(≧2) target molecules are believed to be present, K coupled linear equations in the variable C or the variable $\log_e C$ for these K target molecules are obtained, and the solutions provide most probable values Ck(opt) (k=1 . . . , K) for the concentrations Ck in the gas.

Preferably, Eqs. (17-1) and (17-2) are initially used to estimate the optimum values C1(opt) and C2(opt). If the initial estimate of C1(opt) is found to be at least equal to the first transition value $C1_{tr}$ and the estimate of C2(opt) is found to lie below the second transition value $C2_{tr}$ in FIG. 2, Eqs. (17-3) and (17-4) would be used to redetermine the estimates C1(opt) and C2(opt). If the initial estimates for C1(opt) and for C2(opt) are found to lie below the respective transition values, $C1_{tr}$ and $C2_{tr}$, Eqs. (17-5) and (17-6) would be used to redetermine the estimates C1(opt) and C2(opt). If the initial estimates of C1(opt) and C2(opt) are found to be at least equal to the respective first and second transition values $C1_{tr}$ and $C2_{tr}$, the initial estimates from Eqs. (17-1) and (17-2) would be used, unchanged, for the estimates C1(opt) and C2(opt).

The optimum value estimates, C1 (opt) and C2(opt), however determined, are used to compute error values $$\varepsilon(1; C1(opt)) = \sum_{n=1}^{N} w_n(1)|EPV(n) - EPV(C1(opt); ref1)|^{p1}, \quad (18-1)$$

$$\varepsilon(2; C2(opt)) = \sum_{n=1}^{N} w_n(2)|EPV(n) - EPV(C2(opt); ref2)|^{p2}, \quad (18-2)$$

where $w_n(1)$ and $w_n(2)$ are non-negative weighting values, EPV(n) are the measured EPVs for the N-sensor sub-arrays, EPV(C1) and EPV(C2) are reference EPVs, adjusted for concentrations C1 and C2, for the first and second target molecules, and p1 and p2 are selected positive real numbers.

The optimized error values, $\varepsilon(1;C1(opt))$ and $\varepsilon(2;C2(opt))$, are then compared with selected error threshold values, $\varepsilon(1;thr)$ and $\varepsilon(2;thr)$, respectively, to determine if the target molecule 1 and/or the target molecule 2 is likely to be present in the gas at the concentration C1=C1(opt) and/or at the concentration C2=C2(opt). The formalism set forth in the preceding is extendible to any number M≧1 of different target molecules. At this point, the most probable concentration values, C1(opt) and C2(opt), are determined, but a probability that the target molecules are present with these values is not yet estimated.

Figure 4A:
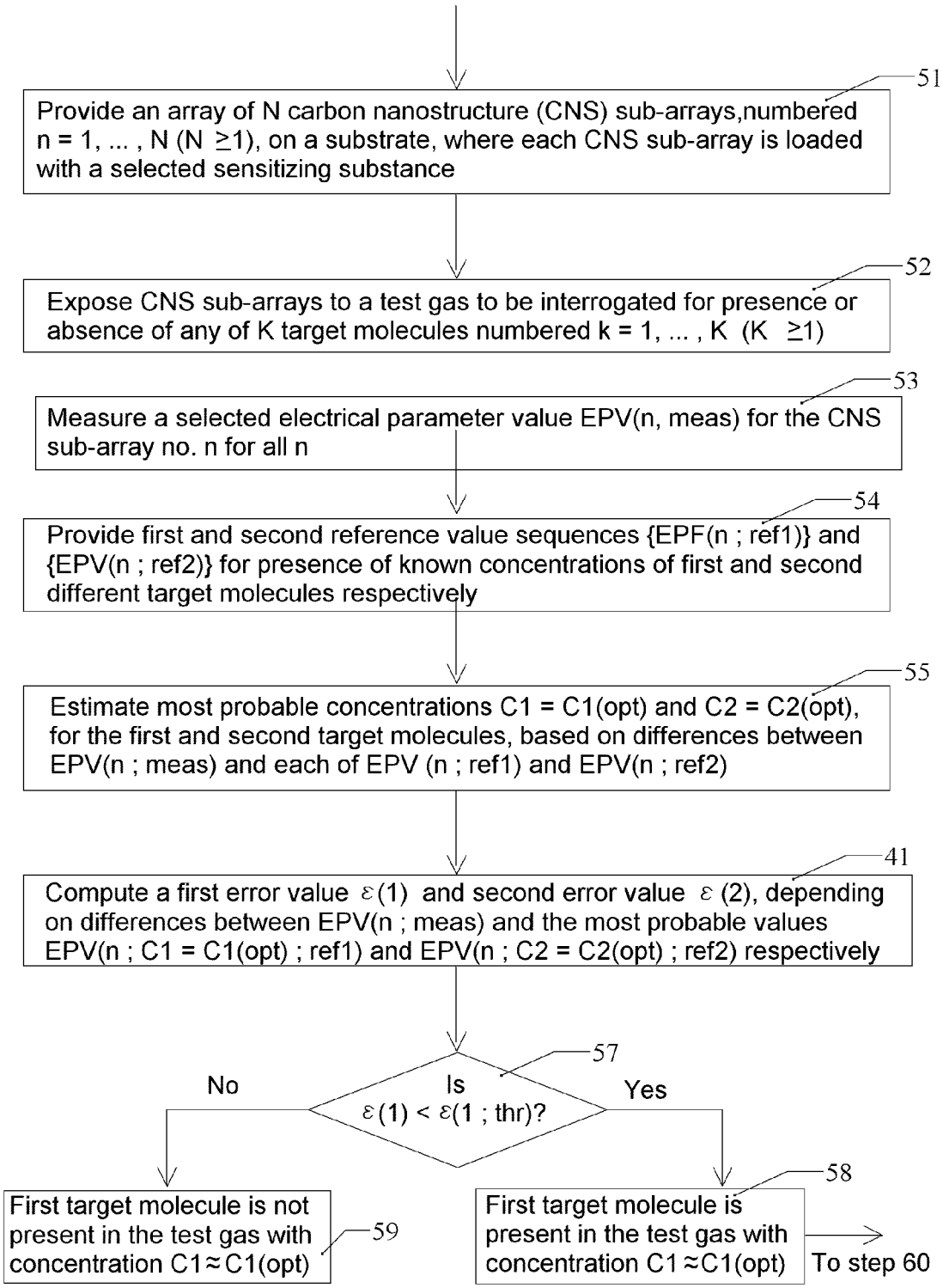
Figure 4B:
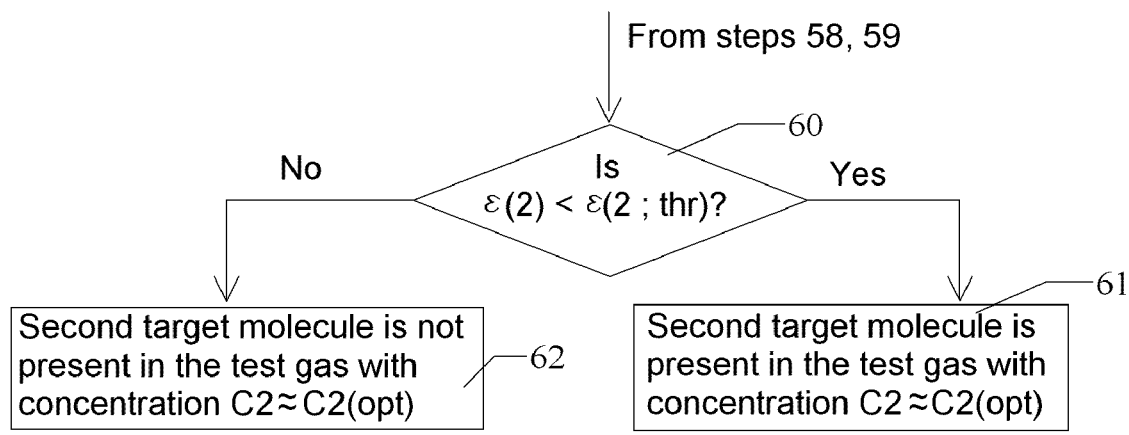

FIG. 4 is a flow chart of a procedure for practicing the invention. In step 51, N sub-arrays (N≧2) of carbon nanostructures ("CNSs") are provided on a substrate, where each CNS sub-array is doped, impregnated, coated or otherwise functionalized ("loaded") with a selected sensitizing substance drawn from a group of substances, for example, Au nanoparticles, associated with other particles. In step 52, the CNS sub-arrays are exposed to a gas to be interrogated (for presence of K different target molecules, with K≧1). In step 53, a selected electrical parameter value EPV(n) for the CNS sub-array no. n is measured in a time interval of length $\Delta t \approx 5-30$ sec or longer if desired. Optionally, the values EPV(n) for all sub-arrays are measured substantially simultaneously.

In step 54, where K=2, a first reference value sequence EPV(n;ref1) and a second reference value sequence EPV(n;ref2) are provided for sub-array no. n, corresponding to presence of first and second different target molecules, present in a gas with known first and second concentration values, C1(ref1) and C2(ref2), respectively.

In step 55, most likely concentrations, C1(opt) and C2(opt), for the first and second target molecules in the test gas are estimated, based upon (1) differences between the N measured values EPV(n) of the collection of CNS sub-arrays and the corresponding reference values EPV(n;C1;ref1) and (2) differences between the N measured values EPV(n) of the collection of CNS sub-arrays and the corresponding reference values EPV(n;C2;ref2), where C1 and C2 are unknown.

At this point, the most-probable concentration values, C1(opt) and C2(opt), for the first and second target molecules are known. In a first embodiment, it is sufficient to estimate the most-probable concentration values for the test gas.

In an extension, an error value is computed, based on differences between the measured values EPV(n) for the N sub-arrays and computed concentration-dependent reference values, EPV(n;C1≈C1 (opt);ref 1) and EPV(n;C2≈C2(opt);ref2), using Eq. (1) or Eq. (3) for the EPV for the first or second target molecule. Only if the first error value (or the second error value) is less than a selected first error threshold value (or less than a selected second error threshold value) is the most-probable concentration value C1=C1(opt) (or C2=C2(opt)) accepted as the concentration value for the first target molecule (or the second target molecule) in the gas. In this extension, the procedures of steps 56-62 are optionally combined with the procedures of steps 51-55.

In step 56, a first error value $\epsilon(1)$ and a second error value $\epsilon(2)$ are computed, depending upon (1) differences between the N measured values EPV(n) of the first CNS sub-array and the corresponding most-probable values EPV(n;C1≈C1(opt); ref1) and (2) differences between the N measured values EPV(n) of the second CNS sub-array and the corresponding most-probable values EPV(n;C2≈C2(opt);ref2).

In step 57, the first error value is compared with a first error threshold value $\epsilon(1;\text{thr})$. In step 58, when the first error value is less than the first error threshold value, the system interprets this condition as indicating that the first target molecule is present in the test gas with a selected first concentration C1≈C1(opt). In step 59, when the first error value is at least equal to the first error threshold value, the system interprets this condition as indicating that the first target molecule is not present in the gas, or is present in the test gas with concentration substantially different from the most-probable concentration, C1≈C1(opt).

In step 60, the second error value is compared with a second error threshold value $\epsilon(2;\text{thr})$. In step 61, when the second error value is less than the second error threshold value, the system interprets this condition as indicating that the second target molecule is present in the test gas with a selected second concentration C2≈C2(opt). In step 62, when the second error value is at least equal to the second error threshold value, the system interprets this condition as indicating that the second target molecule is not present in the test gas, or is present in the gas with concentration substantially different from the most probable concentration, C2≈C2(opt).

Optionally, the system can test for presence of one of K≧2 different target molecules substantially simultaneously. One advantage of the invention is its flexibility: presence of any reasonable number of target molecules can be tested for with a single set of EPV measurements.

Figure 5A:
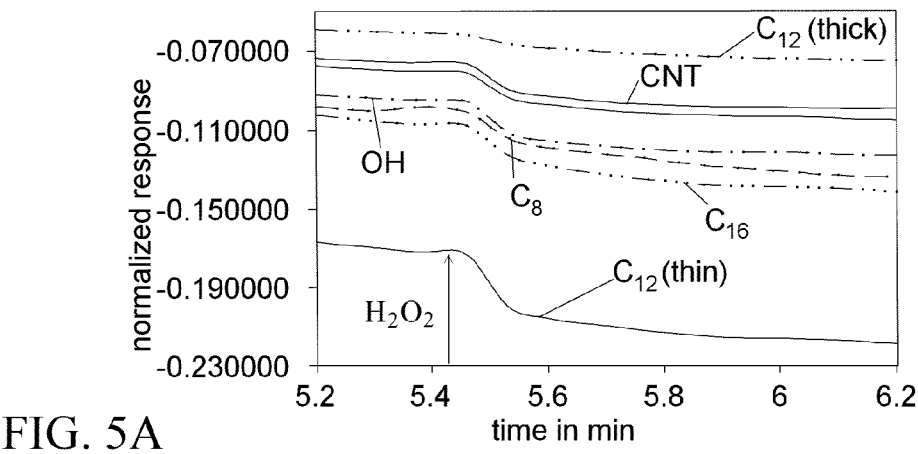
FIGS. 5A, 5B and 5C graphically illustrate normalized responses to selected CNS loadings, before and after exposure to $H_2O_2$, $H_2O$ and $CH_3OH$.
Figure 5B:
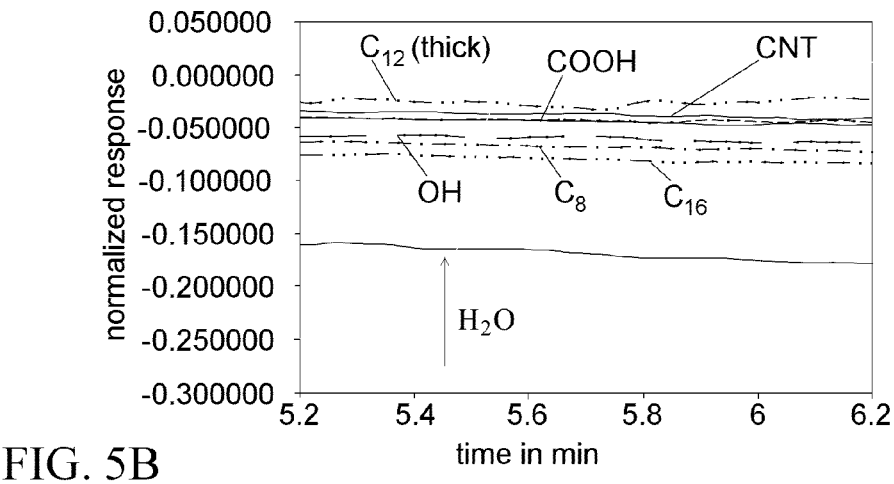
Figure 5C:
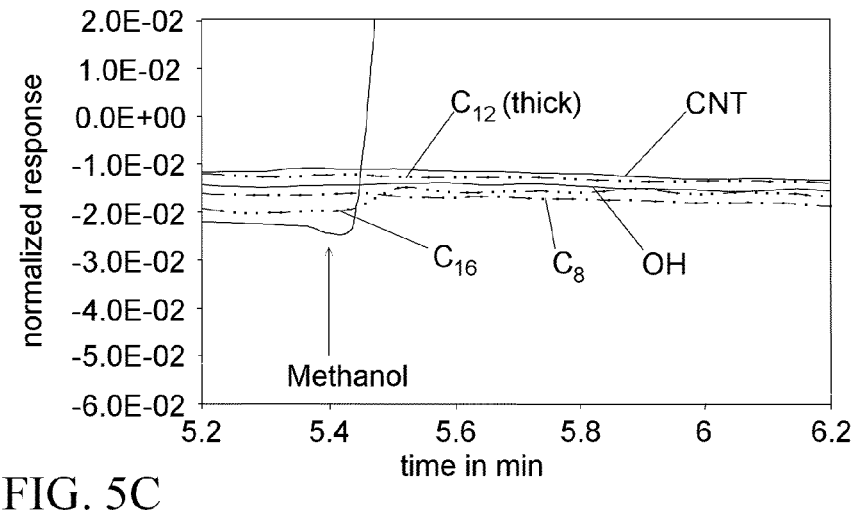

FIGS. 5A, 5B and 5C graphically illustrate measurements of normalized (dimensionless) responses, $$NR(t) = \{R(t) - R_0\}/R_0, \quad (19)$$

of electrical resistance of a loaded CNT, measured before and after introduction of a reference gas $H_2O_2$ (5A), $H_2O$ (5B) and $CH_3OH$ (5C), into a chamber containing the loaded CNT, minus the measured resistance $R_0$ of an unloaded CNT, divided by $R_0$. The curve marked "gas," which rises substantially vertically beginning at a time t≈0.43 min, indicates introduction of the reference gas into the chamber. As an example, the changes in NR(t) for $C_{12}$, measured at times before and after introduction of the reference gas, are measurable: $\Delta NR(t) \approx -0.05$ ($H_2O_2$), ≈−0.02 ($H_2O$) and ≈+0.01 ($CH_3OH$) for the reference gases examined.

Figure 6A:
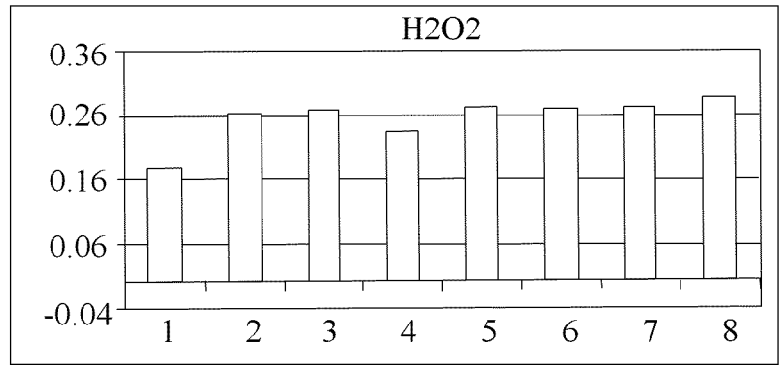
FIGS. 6A, 6B and 6C are histograms of response changes for the respective CNS loadings in FIGS. 5A, 5B and 5C.
Figure 6B:
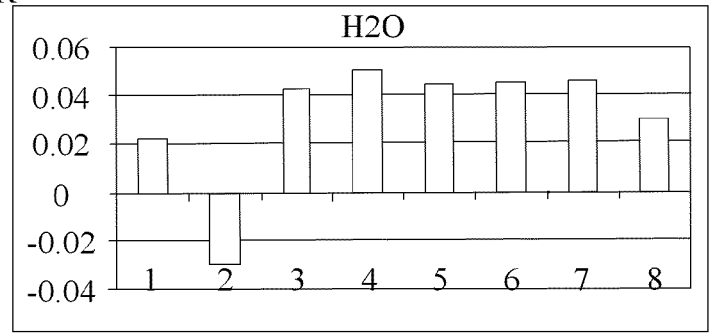
Figure 6C:
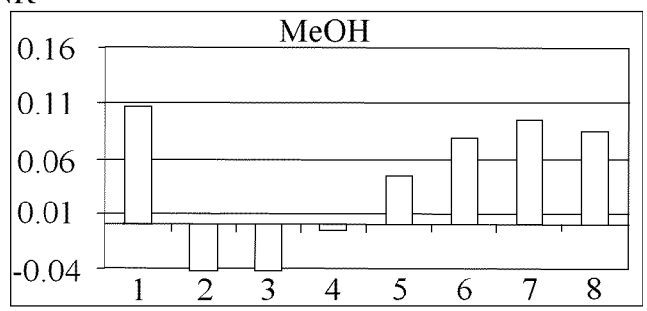

FIGS. 6A, 6B and 6C graphically illustrate histograms representing re-normalized responses for the respective reference gases $H_2O_2$, $H_2O$ and $CH_3OH$, computed as $$NNR\{NR(t;\text{before}) - NR(t;\text{after})\}/NR(t;\text{before}), \quad (20)$$

for 8 sensors among 24 sensors in an embodiment (FIG. 1), where "before" and "after" have the meanings discussed in connection with FIGS. 6A, 6B and 6C. Note that most of the histogram amplitudes are positive, with the exception of the renormalized responses for sensors no. 2, 3 and 4 for $H_2O$ and for $CH_3OH$.

What is claimed is:

1. A method for estimating presence of a target molecule in a gas, the method comprising:

providing N carbon nanostructure ("CNS") sub-arrays, numbered n=1, . . . , N (N≧2) on a substrate, where each CNS sub-array is loaded with a selected sensitizing substance comprising Au nanoparticles;

estimating a first functional relationship EPV(C1;1) between a concentration C1 of a first target molecule and a first measured electrical parameter value EPV(n=1) in a gas, where the first relationship has a first approximate form EPV(n=1)=a1'+b1'·log(C1) in a first concentration range of C1 and has a second approximate form EPV(n=1)=a1+b1·C1 in a second concentration range of C1, where a1', b1', a1 and b1 are selected real numbers;

estimating a second functional relationship EPV(C2;2) between a concentration C2 of a second target molecule and a second measured electrical parameter value EPV(n=2) in a gas, where the second relationship has a third approximate form EPV(n=2)=a2'+b2'·log(C2) in a first concentration range of C2 and has a fourth approximate form EPV(n=2)=a2+b2·C2 in a second concentration range of C2, where a2', b2', a2 and b2 are selected real numbers;

exposing the CNS sub-array no. n (n=1, . . . , N) to the gas, and measuring the electrical parameter value EPV(n) in a time interval of length no more than about 15 sec;

estimating a probable value of concentration, C1(opt) and C2(opt), of the first target molecule and the second target molecule, respectively, in the gas, based upon (1) differences between the value EPV(n=1) and the first functional relationship for the first target molecule and upon (2) differences between the value EPV(n=2) and the second functional relationship for the second target molecule computing a first error value depending upon differences between the measured values EPV(n) of the CNS sub-array no, n=1 and reference values E(C1(opt);ref;n=1) that corresponds to presence of the first target molecule in a gas with a concentration of C1 (opt);

computing a second error value depending upon differences between the measured values EPV(n) of the CNS sub-array no, n=2 and reference values E(C2(opt);ref; n=2) that corresponds to presence of a second target molecule in a gas with a concentration of C2(opt);

when the first error value is less than a selected first error threshold value, interpreting this condition as indicating that the first target molecule is present in the gas with a concentration of about C1(opt);

when the second error value is less than a selected second error threshold value, interpreting this condition as indicating that the second target molecule is present in the gas with a concentration of about C2(opt);

when the first error value is at least equal to the first error threshold value, interpreting this condition as indicating that the first target molecule is not present in the gas or is present in the gas with a concentration substantially less than C1(opt); and when the second error value is at least equal to the second error threshold value, interpreting this condition as indicating that the second target molecule is not present in the gas or is present in the gas with a concentration substantially less than C2(opt).

2. The method of claim 1, further comprising: computing said first error value as a sum $$\varepsilon 1 = \sum_{n=1}^{N} w_n(1)|EPV(n) - E(C1(opt); ref; n = 1)|^{p1},$$

where EPV(n) is said measured parameter value of said first CNS sub-array, EPV(C1(opt);ref1) is a corresponding reference parameter value for said first target molecule, $w_n(1)$ is a non-negative weighting value for said first target molecule, and p1 is a selected positive number.

3. The method of claim 1, further comprising: computing said second error value as a sum $$\varepsilon 2 = \sum_{n=1}^{N} w_n(2)|EPV(n) - E(C2(opt); ref; n = 2)|^{p2},$$

where EPV(n) is said measured parameter value of said second CNS sub-array, EPV(C2(opt);ref 2) is a corresponding reference parameter value for said second target molecule, $w_n(2)$ is a non-negative weighting value for said second target molecule, and p2 is a selected positive number.

4. The method of claim 1, further comprising choosing said electrical parameter value EPV(n) from the group of parameters consisting of electrical impedance, electrical conductance, capacitance and inductance.

5. The method of claim 1, further comprising estimating said first functional relationship where said probable value of concentration C1(opt) is no greater than about 50 ppm.

6. The method of claim 5, further comprising estimating said first functional relationship where said probable value of concentration C1(opt) is no greater than about 5 ppm.

* * * * *